US008938300B2

(12) United States Patent
Rosero (10) Patent No.: US 8,938,300 B2
(45) Date of Patent: Jan. 20, 2015

(54) LEADLESS IMPLANTABLE INTRAVASCULAR ELECTROPHYSIOLOGIC DEVICE FOR NEUROLOGIC/CARDIOVASCULAR SENSING AND STIMULATION

(75) Inventor: Spencer Rosero, Pittsford, NY (US)

(73) Assignee: University of Rochester, Rochester, NY (US)

( * ) Notice: Subject to any disclaimer, the term of this patent is extended or adjusted under 35 U.S.C. 154(b) by 1327 days.

(21) Appl. No.: 11/579,529

(22) PCT Filed: May 4, 2005

(86) PCT No.: PCT/US2005/015374
§ 371 (c)(1),
(2), (4) Date: Jan. 28, 2008

(87) PCT Pub. No.: WO2005/107852
PCT Pub. Date: Nov. 17, 2005

(65) Prior Publication Data
US 2008/0119911 A1     May 22, 2008

Related U.S. Application Data

(60) Provisional application No. 60/567,447, filed on May 4, 2004, provisional application No. 60/567,448, filed on May 4, 2004, provisional application No. 60/567,449, filed on May 4, 2004.

(51) Int. Cl.
*A61N 1/36* (2006.01)
*A61N 1/05* (2006.01)
(Continued)

(52) U.S. Cl.
CPC ........ *A61N 1/05* (2013.01); *A61N 1/362* (2013.01); *A61N 1/372* (2013.01); *A61N 1/375* (2013.01); *A61N 1/37205* (2013.01); *A61N 1/37288* (2013.01); *A61N 1/3756* (2013.01)
USPC .............................................. 607/45; 607/36

(58) Field of Classification Search
USPC ....................... 607/2, 9, 36, 62, 45
See application file for complete search history.

(56) References Cited

U.S. PATENT DOCUMENTS 3,554,187 A    1/1971   Glassner et al.
3,760,332 A    9/1973   Berkovits et al.
(Continued)

FOREIGN PATENT DOCUMENTS

WO    WO 98/02209     1/1998
WO    WO-98/26840    6/1998
(Continued)

OTHER PUBLICATIONS

Daniel A. Leung et al., Selection of Stents for Treating Iliac Arterial Occlusive Disease, Feb. 2003 JVIR, pp. 137-152, vol. 14, No. 2.
(Continued)

*Primary Examiner* — George Evanisko
(74) *Attorney, Agent, or Firm* — Patent Technologies, LLC; Robert O. Gunderman, Jr.

(57) ABSTRACT

A leadless intravascular sensor (100, 200) uses the body tissue as a communication medium. The implantable intravascular device has a tubular stent-like structure (102) for intravascular fixation with embedded microcircuits to allow bipolar and unipolar sensing of cardiac and neurologic electrical activity, sensing of other physiologic signals, local electrical stimulation (cardiac pacing and defibrillation; neurologic stimulation and seizure therapy) as well as the ability to communicate with other implanted and non implanted devices via radio frequency and/or optical communication and/or analog signal communication using body tissue as the conducting medium. The device can also be used in the extravascular or perivascular space. In this form, it has an open/flexible ring that can be adjusted, or self-adjusts to provide no pressure or required contact around the vessel or target region.

11 Claims, 3 Drawing Sheets

(51) Int. Cl.
*A61N 1/362* (2006.01)
*A61N 1/372* (2006.01)
*A61N 1/375* (2006.01)

(56) References Cited

U.S. PATENT DOCUMENTS

| | | | |
|---|---|---|---|
| 3,842,842 A | 10/1974 | Kenny et al. |
| 3,943,936 A | 3/1976 | Rasor et al. |
| 4,124,029 A | 11/1978 | Penn |
| 4,248,237 A | 2/1981 | Kenny |
| 4,987,897 A | 1/1991 | Funke |
| 5,154,172 A | 10/1992 | Terry, Jr. et al. |
| 5,188,104 A | 2/1993 | Wernicke et al. |
| 5,207,709 A | 5/1993 | Picha |
| 5,215,086 A | 6/1993 | Terry, Jr. et al. |
| 5,331,966 A | 7/1994 | Bennett et al. |
| 5,331,996 A | 7/1994 | Ziehm |
| 5,351,394 A | 10/1994 | Weinberg |
| 5,358,514 A | 10/1994 | Schulman et al. |
| 5,404,872 A | 4/1995 | Choi |
| 5,411,535 A | 5/1995 | Fujii et al. |
| 5,674,251 A | 10/1997 | Combs et al. |
| 5,707,400 A | 1/1998 | Terry, Jr. et al. |
| 5,814,089 A | 9/1998 | Stokes et al. |
| 5,987,352 A | 11/1999 | Klein et al. |
| 6,011,984 A | 1/2000 | Van Antwerp et al. |
| 6,047,214 A | 4/2000 | Mueller et al. |
| 6,117,643 A | 9/2000 | Simpson et al. |
| 6,120,460 A | 9/2000 | Abreu |
| 6,141,588 A | 10/2000 | Cox et al. |
| 6,168,243 B1 | 2/2001 | Brown |
| 6,264,941 B1 | 7/2001 | Baetge et al. |
| 6,330,481 B1 | 12/2001 | Van Wijk et al. |
| 6,409,675 B1 | 6/2002 | Turcott |
| 6,412,490 B1 | 7/2002 | Lee |
| 6,423,001 B1 | 7/2002 | Abreu |
| 6,438,427 B1 | 8/2002 | Rexhausen et al. |
| 6,442,413 B1 * | 8/2002 | Silver | 600/345 |
| 6,445,953 B1 | 9/2002 | Bulkes et al. |
| 6,480,733 B1 | 11/2002 | Turcott |
| 6,496,715 B1 | 12/2002 | Lee et al. |
| 6,512,949 B1 | 1/2003 | Combs et al. |
| 6,522,915 B1 | 2/2003 | Ceballos et al. |
| 6,522,926 B1 | 2/2003 | Kieval et al. |
| 6,527,729 B1 | 3/2003 | Turcott |
| 6,537,256 B2 | 3/2003 | Santini, Jr. et al. |
| 6,551,243 B2 | 4/2003 | Bocionek et al. |
| 6,560,486 B1 | 5/2003 | Osorio et al. |
| 6,564,106 B2 | 5/2003 | Guck et al. |
| 6,584,352 B2 | 6/2003 | Combs et al. |
| 6,600,949 B1 | 7/2003 | Turcott |
| 6,616,624 B1 | 9/2003 | Kieval |
| 6,622,046 B2 | 9/2003 | Fraley et al. |
| 6,647,292 B1 | 11/2003 | Bardy et al. |
| 6,650,919 B2 | 11/2003 | Edelberg et al. |
| 6,656,162 B2 | 12/2003 | Santini, Jr. et al. |
| 6,721,587 B2 | 4/2004 | Gough |
| 6,721,597 B1 | 4/2004 | Bardy et al. |
| 6,733,485 B1 * | 5/2004 | Whitehurst et al. | 604/500 |
| 6,850,801 B2 | 2/2005 | Kieval et al. |
| 6,856,835 B2 | 2/2005 | Bardy et al. |
| 7,734,343 B2 * | 6/2010 | Ransbury et al. | 607/4 |
| 2002/0019584 A1 | 2/2002 | Schulze |
| 2002/0095191 A1 | 7/2002 | Bulkes et al. |
| 2002/0099273 A1 | 7/2002 | Bocionek |
| 2002/0183791 A1 | 12/2002 | Denker et al. |
| 2002/0198473 A1 | 12/2002 | Kumar |
| 2003/0036683 A1 | 2/2003 | Kehr |
| 2003/0153818 A1 | 8/2003 | Bocionek |

FOREIGN PATENT DOCUMENTS

| | | | |
|---|---|---|---|
| WO | WO98/43700 | * 10/1998 |
| WO | 2004/030706 A2 | 4/2004 |
| WO | 2009/002209 A1 | 12/2008 |

OTHER PUBLICATIONS

TechWeb: TechEncyclopedia, The Computer Language Company, pp. 1-4, copyright 1981-2005, accessed at http://www.techweb.com/encyclopedia/defineterm.jhtml?term=MEMS on Apr. 21, 2005.

Medtronic Vascular—Racer Over-the-Wire Biliary Stent System, pp. 1-6, accessed at <http://www.medtronic.com/medtronic_vascular/ps_racer.html on May 4, 2005.

Vascular Stent, Endovascularone.com: Official Homepage of Endovascular Center, pp. 1-3, accessed at http://www.endovascularone.com/vs.htm on May 3, 2005.

Medtronic Vascular-Bridge Extra Support Renal Stent System, pp. 1-3, accessed at http://www.medtronic.com/medtronic_vascular/ps_es.html on May 4, 2005.

* cited by examiner

LEADLESS IMPLANTABLE INTRAVASCULAR ELECTROPHYSIOLOGIC DEVICE FOR NEUROLOGIC/CARDIOVASCULAR SENSING AND STIMULATION

RELATED APPLICATIONS

This application is a National Phase Entry of PCT/US2005/015374 filed May 4, 2005, which claims priority to provisional application Ser. Nos. 60/567,447, 60/567,448 and 60/567,449, each filed on May 4, 2004, and which are all hereby incorporated by reference in their entirety.

TECHNICAL FIELD

The present invention is generally related to intravascular and extravascular devices for sensing and stimulation, and more particularly, to an implantable intravascular device that allows for the sensing of cardiac, neurologic and physiologic activity, provides local electrical stimulation, and communicates with other implantable and non-implantable devices via leadless communication using radiofrequency communication, ultrasonic communication, and/or body tissue as a conducting medium.

BACKGROUND OF THE INVENTION

The use of implantable medical devices to treat a variety if diseases is growing due to the rapid advances in technology. Diseases that disrupt the ability of the heart, brain, or nervous system to communicate or function normally include heart rhythm disorders such as ventricular fibrillation, heart block, and neurologic disorders such as epilepsy, multiple sclerosis, spinal injury, and dysautonomias. Drug and pharmacologic therapy have been used to treat these disorders, and pacemakers and defibrillators have been used to treat heart rhythm disorders. As shown in U.S. Pat. Nos. 5,351,394, 5,215,086, 5,188,104, 5,154,172 and 5,707,400, treatments for deep brain stimulation include the use of wires within the brain with implantable devices to stimulate target areas of the nervous system in order to control epilepsy, hypertension, as well as movement disorders such as Parkinson's disease.

Surgical procedures have also been used to treat these disorders. For example, open brain surgery for the placement of leads such as wires that are positioned through brain tissue to reach target sites that are tunneled under the skin to a device implanted elsewhere: and placing wires in the heart to provide a defibrillation shock (established procedure) using the blood vessels as the conduit to reach the heart.

The mode of brain and heart regulation via electrical impulses has been well known for decades and is the basis for today's pacemakers, defibrillators, and deep brain stimulation devices, as mentioned in the above referenced patents. Defibrillation and cardioversion are techniques employed to counter arrhythmic heart conditions including some tachycardias in the atria and/or ventricles. Fibrillation is a condition where the heart has very rapid shallow contractions and, in the case of ventricular fibrillation, may not pump a sufficient amount of blood to sustain life. A defibrillator often is implanted in the chest cavity of a person who is susceptible to reoccurring episodes of ventricular fibrillation. Typically, electrodes are employed to stimulate the heart with electrical impulses or shocks, and are of a magnitude substantially greater than the magnitude of pulses used in cardiac pacing. The implanted defibrillator senses a rapid heart rate during fibrillation and applies a relatively high energy electrical pulse through wires connected to electrodes that are in turn attached to the exterior wall of the heart.

Examples of ECG sensors are shown, for instance, in U.S. Pat. Nos. 6,412,490 and 5,987,352. Examples of pacemakers are shown, for instance, in U.S. Pat. Nos. 3,554,187; 3,760,332; 3,842,842; 4,248,237; and 4,124,029. The technologies described in those patents are, however, hampered by the use of a transvenous lead for electrophysiologic stimulation. In those technologies, a transvenous/vascular access is required for intracardiac lead placement. Those technologies are also susceptible to an acute risk of cardiac tamponade, perforation of the heart or vasculature and long term risk of endocarditis or a need for intracardiac extraction of the lead due to failure. Also, current technologies present a problem for intracardiac defibrillation implantation in younger patients or in patients who are otherwise not candidates for the implantation because of anatomical abnormalities. Complex steps and risks are involved in obtaining venous vascular access and placement of the transvenous lead in the patient population requiring defibrillation.

Delivering electrical sensing and stimulation leads to specific areas of the brain is difficult. The skull must be opened and the brain exposed, the leads are then inserted through normal brain tissue in order to reach the abnormal section, and then the leads are tunneled under the skin often to the chest area where a device is connected to the lead(s). The risk of infection is high because of the resultant contact of the inner brain areas with areas close to the surface of the skin via the lead. In addition, normal brain tissue is disrupted in the process, and any complication or infection often requires that the whole implanted system be removed.

Given the risks associated with these current procedures, aa well as the limitations that arise when devices must use a lead to reach the target site, there is a need for a new approach using implantable electronic medical devices that are wireless for the treatment of heart, brain, and nervous system disorders.

SUMMARY OF THE INVENTION

An implantable intravascular device is disclosed that has a stent-like structure for intravascular fixation with embedded microcircuits to allow for bipolar and unipolar sensing of cardiac and neurologic electrical activity, sensing of other physiologic signals, local electrical stimulation (such as cardiac pacing and defibrillation; neurologic stimulation of brain and specific nerve sites and seizure therapy) as well as the ability to communicate with other implanted and non implanted devices via radio frequency and/or optical communication and/or analog signal communication using body tissue as the conducting medium.

The device can react to physiologic signals it senses and provide electrical stimulation in response to the detected physiologic signals. The electrical stimulation can be used for various purposes, such as regulating the heart and nervous system, stimulating the heart to beat or return to a normal rhythm, stimulating the brain back to normal activity during a seizure episode (epilepsy), providing relief of pain by local nerve stimulation, and controlling blood flow at various parts of the body by local and central nervous system stimulation. The device communicates information to other implanted and non-implanted devices that can then act on the information received. For example, information can be transmitted to an infusion pump (implanted or external), which uses the information to inject insulin to control diabetes, release anti-arrhythmic drugs for heart rhythm control, or release anti-seizure medication when a seizure is detected. The combination of local data transmission via biologic tissue coupled with wireless communication enhances the specificity and integrity of the data being transmitted by reducing noise and artifacts.

The device can also be used in the extravascular or perivascular space. In this form, it has an open and flexible ring that can be adjusted, or self-adjusts to provide no pressure or required contact around the vessel or target region. In this form, the device is positioned using minimally invasive instruments that allow for a small surgical incision, through which tools are designed to position the device at the target site. Fiber optic visualization is used to find the target site and place the device at that position. The extravascular form of the present invention does not necessarily have the size limitations required of an intravascular device, whose size is determined by the vessel's diameter. Accordingly, the extravascular embodiment of the device allows for the attachment of probe modules having flexible inert materials that are used for complex sensing, conducting, or form an antennae for larger geographic operations to provide additional functionality. Those attachments may be made by use of a string or coil and can be placed for easy removal without requiring removal of the perivascular device.

The device, when placed within a vessel, can also record the pressure imposed by the vessel wall (pressure transducer) and respond accordingly. For example, specific vessels may constrict in response to physiologic stimuli including blood flow changes within the region. This pressure can be detected by the device and information relayed to a controller or another similar device. In addition, the devices can be networked with one another and with an optional controller, and their stimulation pulses or energy delivery coordinated between them to provide the desired response by the biologic tissue. For example, if a seizure is starting in one particular site in the brain, the devices can detect the region and begin to treat while other devices can emit low or high energy signals that are synchronized and protect the normally functioning parts of the brain by making them refractory to the epilepsy electrical activity.

BRIEF DESCRIPTION OF THE DRAWINGS

FIGS. 6-8 are perspective views of the extravascular device secured to a vessel;

DETAILED DESCRIPTION OF THE PREFERRED EMBODIMENTS

In describing a preferred embodiment of the invention illustrated in the drawings, certain specific terminology will be used for the sake of clarity. However, the invention is not intended to be limited to that specific terminology, and it is to be understood that the terminology includes all technical equivalents that operate in a similar manner to accomplish the same or similar results.

Figures 1A, 5A:
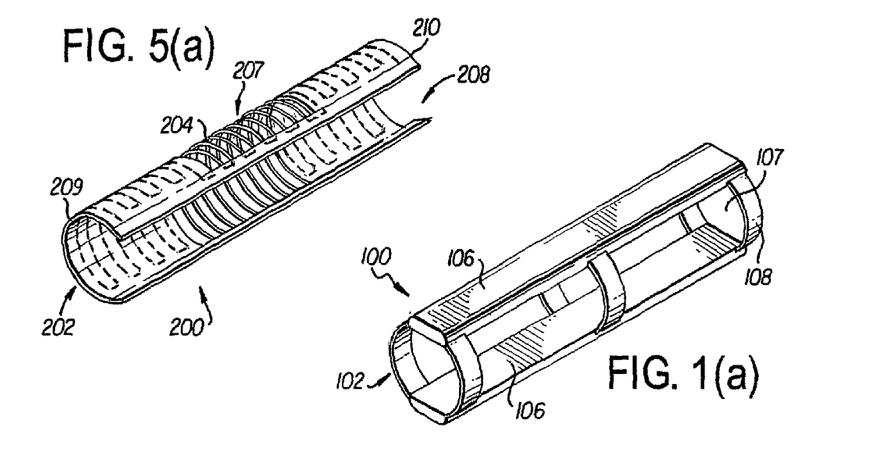
FIGS. 1(a) and 1(b) are perspective drawings of the intravascular sensor and stimulation device.
FIG. 5(a) is a perspective view of the extravascular sensor and stimulation device 10.
Figures 8, 10:
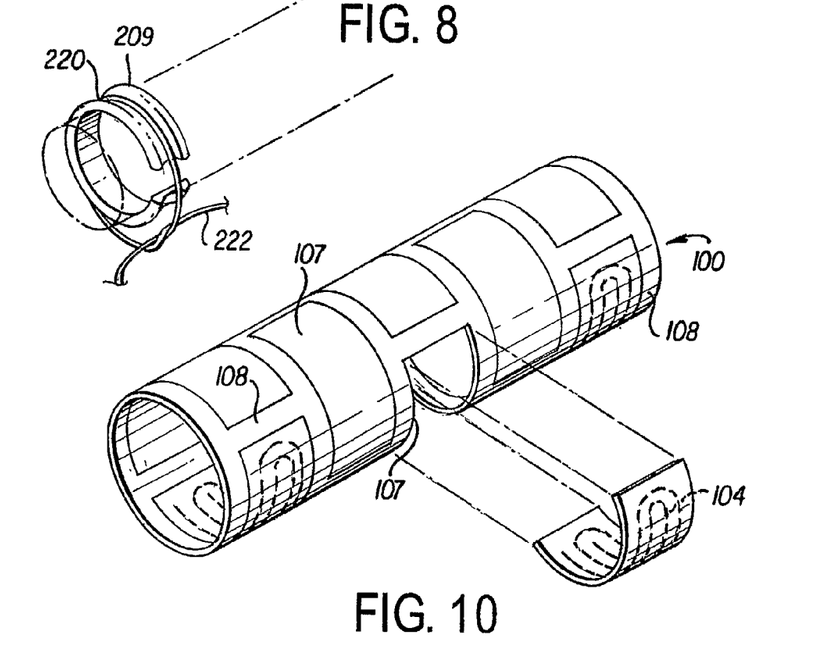
Figure 9:
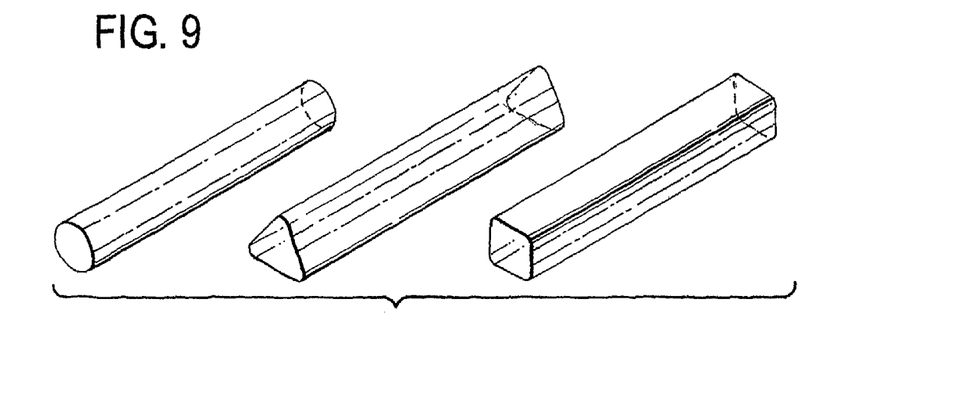
FIG. 9 is a perspective view showing alternative embodiments of the present invention; and, FIG. 10 is a perspective view of an intravascular device in which a panel (representing a space between the structural bands) is pulled out to show positioning of the coil.

Referring to the drawings, FIGS. 1(a), (b) and 5(a), (b) show sensing and stimulation devices 100, 200 in accordance with preferred embodiments of the invention. The devices 100, 200 are generally tubular in shape and have a support structure 102, 202, an induction power coil 104, 204 built into the support structure 102, 202, and electronic components 106. The device 100 can be intravascular, as shown in FIGS. 1-4, or extravascular, as shown in FIGS. 5-8. Though the device 100, 200 is shown as having an elongated round tubular shape, it can also have a triangular or square shape, as shown in FIG. 9. The devices 100, 200 are configured to be placed at various target sites, such as vessels, nerves, and organs.

The coil 104 is integrated with the support structure 102 by using a continuous insulated metallic wire to provide a loop for inducing current. The coil 104 receives RF energy from a separate device, such as a standard pacemaker or defibrillator to which an induction coil has been added or a dedicated device that is implanted nearby, to produce an electrical power supply for the intravascular device 100.

Figures 1B, 5B:
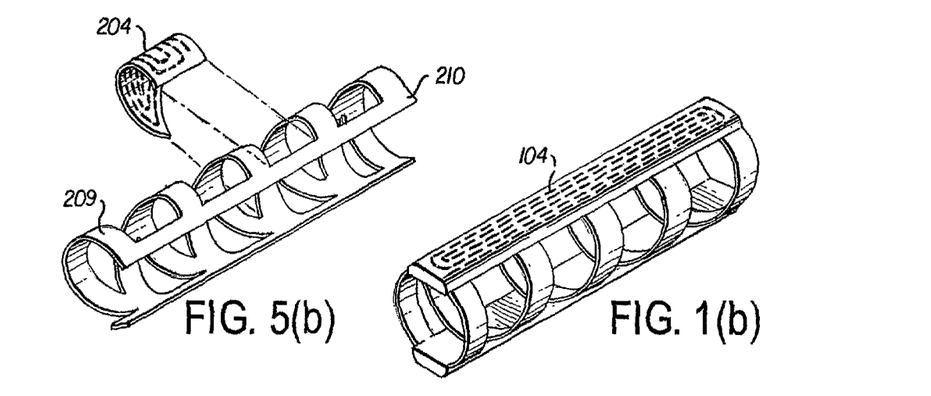
FIG. 5(b) is a perspective view of an extravascular device in which a panel (representing a space between the structural bands) is pulled out to represent positioning of the coil.

The induction coil 104 is fashioned in a manner that maximizes its length, thereby increasing the resulting power supplied by the coil 104. For instance, the coil 104 can be looped like a telephone cord coil by wrapping it around the structure along the length of the device 100. In the intravascular device of FIGS. 1(a), (b), the wire can be extended around the support struts 108, regardless of their shapes. Since the coil is metallic, it also provides a platform for the device structure. The coil 104 can be affixed to the support structure by virtue of its intersection shapes, or it can be adhered by glue, or welded. The electronics 106 can either be attached to, or integral with, the coil 104 or to the struts or bands 108. The coil 104 can be placed on the bands 108, or inlaid at the spaces 107 between the bands 108.

There are numerous possible embodiments of the support structure that are suitable for use with the invention as will be apparent from this disclosure. The structures 102, 202 of FIGS. 1, 5, and 10 show a basic uncomplicated design that are merely exemplary. More complicated designs can also be used, such as one having bands 108 that are generally flat and formed to have an S-shape, crossing patterns, or curving repeating patterns. For instance, one suitable design having a complex pattern is known as the "Palmaz Corinthian." The structure 102, 202 can be laser cut or etched, woven, knitted, coiled, or welded in construction.

The coil 104 preferably follows the general contour of the bands 108. For instance, as shown in FIG. 5 (for the extravascular device 200) and FIG. 10, a continuous coil 104, 204 can be positioned along the entire device 100 in the spaces 107, 207 between the bands 108, 209 and/or extending over the bands 108. As a further example with respect to the Palmaz Corinthian design, the coil can be positioned along the various bands in accordance with that pattern. The coil can also be positioned in the spaces between the bands in that design to mimic that pattern within those spaces. The coil positioned in those spaces can be attached to the bands, for instance, by being wrapped around various intersections with the band or by adhesion.

Figures 2, 3A, 3B:
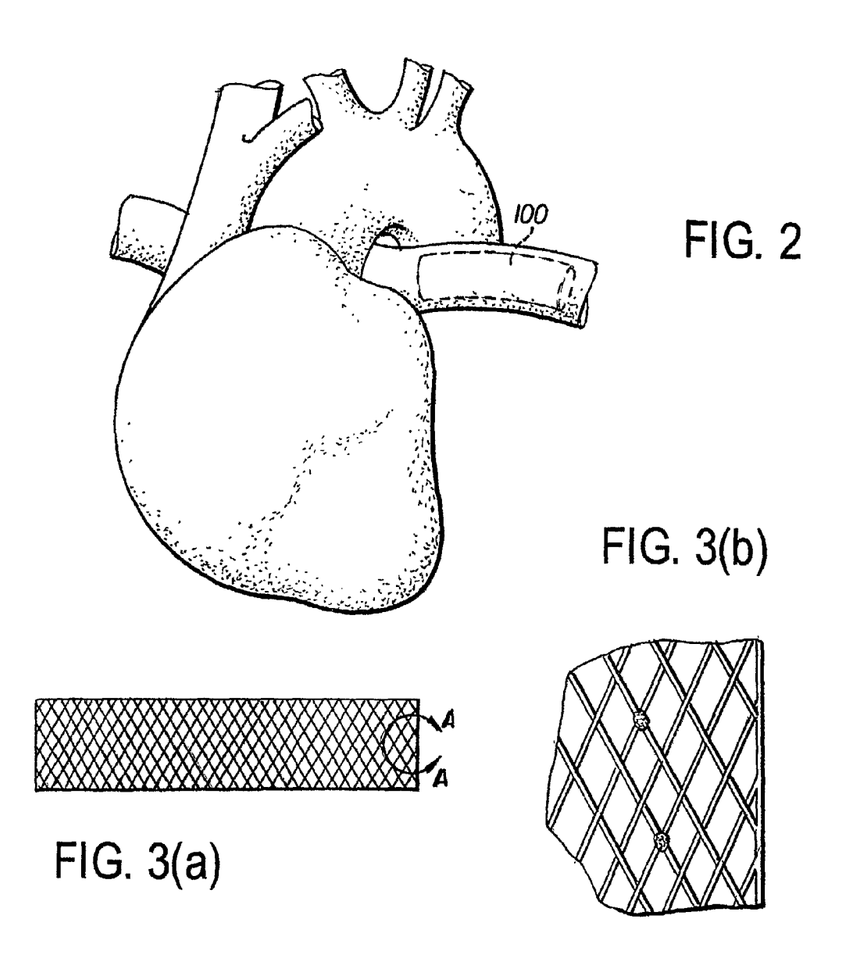
FIG. 2 depicts the intravascular device positioned in a vessel of the body.
FIG. 3(a) is a side view of the coil used with the intravascular device.
FIG. 3(b) is an exploded view of the coil shown in FIG. 3(a) taken about line A.

FIGS. 3(a), (b) show one example of the coil 104 for use with the device 100 of FIG. 1(a). The coil 104 forms a crossing pattern that allows the coil 104 to compress and expand. The coil 104 can be configured over the struts 108 and the electronics 106 secured on top of the coil 104. Or, the electronics 106 can be secured to the struts 108 and the coil 104 positioned over the top of the electronics 106. As shown in FIG. 3(*b*), the mesh has contact points where electrical continuity is provided for a particular application. The struts 108 can be metallic strut components that are electrically isolated from the induction coil structure by insulated contact points so that, although metallic, continuity is maintained with the use of insulation between functional support portions of the strut and the surrounding conductor cable/wire.

The contact points mechanically and electrically insulate the strut 108 from the coil 104. The coil is wrapped in an insulating coating except for the contact points to facilitate electrode detection if the induction coil wiring is used for electrode sensing or to run separate wiring to the electrodes that are carried over the struts or meshed within but not in direct contact with the surrounding metal. As shown in FIG. 1(*b*), the coil 104 can also be configured to be relatively flat and positioned on top of the electronics 106.

The induction power coil 104 is configured in a manner that it remains flexible to avoid fracture and also to facilitate placement, especially at target areas that are curved. The coil 104 is made of titanium alloy, nitinol, tantalum, platinum, stainless steel, or metal alloys, which allow electrical current to flow. The coil 104 material and pattern are configured to be flexible so that the device 100 can be compressed for delivery. The coil 104 material and pattern must also be able to remain sufficiently rigid so that the device 100 does not become dislodged once it is expanded in position. Thus, the device 100 is configured to be collapsible to a size smaller than the final opened diameter. The coil 104 is aligned along the longitudinal aspects of the device and can not collapse, and is made with a low profile (thin). The connections can be designed with pliable inter-component material, such as rubber or silicon, to form joints between the components to provide added flexibility.

The flexibility and compressibility of the device 100 allows target sites to be reached. The device 100 is compressed and delivered to a target site. Once in position, the device 100 is expanded, either by use of a balloon or a drive shaft controlled by the delivery system. This miniaturization also allows for smaller incisions and minimal disruption of tissue. When the intravascular device 100 is expanded, at least one part of it is slightly larger than the target site in which it is positioned, so that the device 100 remains fixed in its position without becoming dislodged. For instance, the electronics 106 can press against the walls of the target site. Though the device 100 has a tubular (stent-like) shape, it is designed for intravascular fixation, and not for opening up blocked vessels, or keeping vessels opened. Once the device 100 is expanded, it is locked and will not collapse. Accordingly, though the structure 102 of the device 100 need not have the ability to open up blocked vessels or keep them opened, the structure can also provide that function.

As further shown in FIGS. 1(*a*), (*b*), the device 100 has electronic components 106 that extend along the length of the support structure 102 in the longitudinal direction at opposing sides of the tubular body. The electronic components 106 are microcircuits that may include, for instance, a capacitor, battery, antenna, and a communications device such as a wired or wireless transceiver. Microcircuits can be placed anywhere around the structure of the device 100, as long as the device 100 remains flexible and can be affixed within the patient. The antenna can alternatively be integrated into the metallic structure of the struts 108 by being woven into the strut 108 or attached to the strut 108. The struts 108 can also be designed to use the same struts/coils for power supply at times and RF communication transmitting/receiving at other times. For instance, electronic switches or relays can be provided that can connect an RF circuit and a sensing circuit in an alternating intermittent fashion. The device 100 can also have a small microprocessor to store data.

The struts 108 may also comprise electrodes or sensors that contact with the surfaces of the target sites. Alternatively, the electrodes may be a band on the outside of the coil that enters the device through a gap in the coil and is insulated to protect against contact with the coil. Preferably, there are three electrodes, one at each end of the device 100 and one at the middle of the device 100. More or fewer electrodes can be used, though at least two should be provided to measure electrical activity. Three electrodes are preferred so that smaller signals can be sensed and a stimulus can be delivered at different sites by inducing a voltage across the target tissue between the electrodes. As shown, the sensors 108 are preferably formed in the shape of a circular band, which allows for the entire circumference of the sensor to be in contact with the target site wall. The device can also function without a sensor by providing a stimulation pulse in response to a command generated by other devices that are either external or implantable. The intravascular placement of the device 100 only results in a minimal disruption of fluid flow within the targeted region. Though the device has been described for use with vessels, other conduits are also suitable, such as the intestines or arteries.

Figure 4:
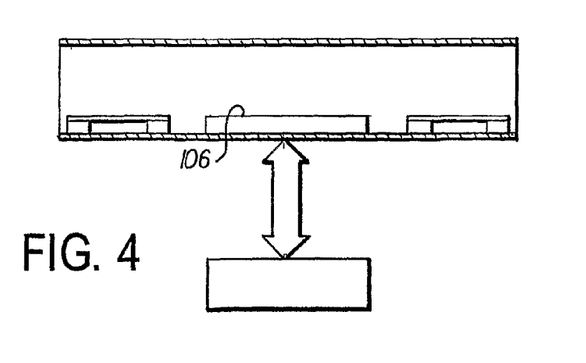
FIG. 4 is a side cutaway view of the intravascular device having electronic components at the interior of the device.

As shown in FIGS. 1(*a*), (*b*), the electronic components 108 can be positioned on the exterior side of the device 100. However, the electronic components 108 can also be positioned at the interior side of the device 100, as shown in FIG. 4. Though this may impede the flow of fluid, it may be acceptable for certain applications, such as for use with blood vessels that are not in critical areas. In addition, the device 100 can be made even smaller if a solid center can be used for a particular application.

FIGS. 5(*a*), (*b*) show the device 200 in accordance with other preferred embodiments of the invention. Here, the device 200 is utilized in the extravascular or perivascular space. The extravascular stimulation and/or sensing device 200 is configured to lock in place at the outside of a vessel, nerve, or organ without damaging that target site. The extravascular device 200 has a support structure 202 and a longitudinal opening 208. The support structure 202 includes one or more flexible bands 209 that are connected together by a leading edge 210. The coil 204 is configured so as not to obstruct the opening 208. The length of the coil 204 is maximized by folding the coil 204 back and forth along the support band 209. The coil 204 can be woven to extend the gaps located between the bands 209. Since the extravascular device 200 is not delivered intravascularly, size is less of an issue and the device 200 need not be compressible.

The opening 208 allows the device 200 to be placed around the outside of nerve bands, vessels, or organs. Preferably, the extravascular device 200 is adjustably secured and is able to decrease the lumen diameter of the c-clamp to allow good contact between the sensors or electrodes and the target tissue (nerve or blood vessel). The opening 208 can be slightly narrower than the target site, so that upon placement it is pried open and retracts back around the vessel when released by the physician and then secures automatically. The device 200 can be used to stimulate nerve bundles, localized areas of the brain or measure flow within the vessels it is attached to without having it within the vessel.

Figures 6, 7:
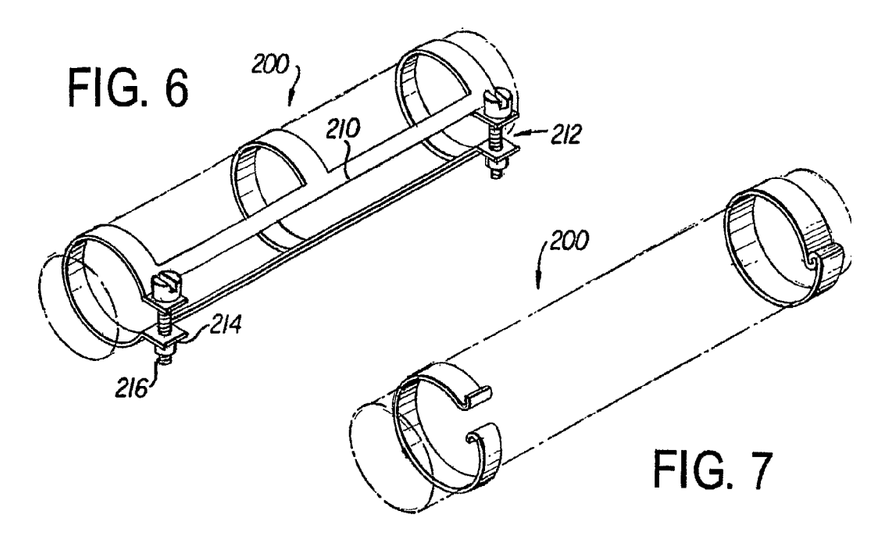

Alternatively, the opening 208 can be wider than the target site so that the device 200 can be positioned and then clamped to the vessels, as with FIGS. 6-8. Referring to FIG. 6, the leading edges 210 of the support structure 202 have one or more retention mechanisms 212 positioned along the length of the device 200. A ledge 214 extends outward from each of the leading edges 210 substantially parallel to one another. A screw 216 extends between the ledges 214 to close the device about the target site. In FIG. 7, at least one portion of the leading edges 210 are formed as a mating clasp. Accordingly, the leading edges 210 clasp together to close the device about the target site. In FIG. 8, the band 209 is configured with a groove 220 that receives a string 222. Still yet, the extravascular device 200 can be sutured to the target site.

The device 100, 200 has good contact with the surrounding tissue so that electrical signals can be recorded and stimulation imparted. The extravascular device 200 also allows for the attachment of probe modules having flexible inert materials. The probe modules are add-on accessories that have a microcircuit chip to provide firmware or software capabilities for more sophisticated operations. The probe module can also be a dedicated sensor with special functions for further individualization or customizing of the device. The probe modules can be used for complex sensing, conducting, or form an antennae for larger geographic operations. The probe modules may be in the form of a small box or a thin plate string or coil if extended antennae or sensing is needed and can be placed for easy removal without requiring removal of the perivascular device.

The device 100, 200 can be used as a leadless implantable physiologic sensor with emphasis on cardiac physiology and neurophysiologic systems. Its application allows placement of physiologic sensors/electrical devices in any area of the body that has blood vessels or can be safely reached via a vascular/minimally invasive surgical procedure. For instance, the device 100, 200 can be placed with the cardiac venous circulation via coronary sinus and epicardial coronary veins (for the epicardial veins, the device is intravascular, though it can also be outside the heart) to sense and transmit cardiac rhythm signals such that the electrocardiogram may include depolarization as well as repolarization data, dynamic intra cardiac beat signals such as repolarization duration, epicardial repolarization alternans frequencies (indirect T wave alternans measurements), and heart rate variability. The electronics 106, 206 can be configured to provide the operation and capabilities of surface electrocardiograms, such as those in U.S. Pat. Nos. 5,987,352 and 6,412,490, and in PCT publication No. WO98/02209.

Thus, in accordance with a preferred embodiment, the device 100, 200 does not have a traditional power supply (i.e., a battery), but instead the induction coil 104, 204 receives power from an external device or another implanted device, such as shown in FIG. 5. The power supply can be provided for example by a combination of the blood flow itself using the support as an induction coil, or a local micro-capacitor combined with a small subcutaneous generator/controller unit. A separate transmitter can also be used to generate RF energy which is received by the induction coil 104, 204 in the separate device and induces a current by way of the power supply that powers the device 100, 200. The transmitter can be external to the patient or placed under the skin where it can easily be replaced. Alternatively, however, power can be supplied by a rechargeable battery. A capacitor can also be provided to store energy to deliver a stimulation pulse as well as for communication.

In addition to sensing the electrophysiologic signals, the device 100, 200 can, because of its location within the functional vasculature, provide fluid or blood flow and hemodynamic measurements as well as blood components/chemical sensing in a dynamic manner (i.e., oxygen saturation, glucose, neurohormonal levels, pH, neuropeptide, etc.) via a variety of methods that can incorporate electrical, temperature, and optical sensing, such as a temperature probe, pH probe, glucose monitor, or oxygen saturation monitor. It can also measure temperature changes between each of its ends to calculate blood flow in the heart or blood vessels. It can also measure pressure and change of position or movement, such as by way of an accelerometer for the beating heart or peristalsis movement of the gastrointestinal tract.

Still further, the device 100, 200 can be utilized to pace (i.e., electrodes) and/or stimulate biologic tissue (heart, brain, central/peripheral nervous system, gastrointestinal system). It can deliver high energy, rapid electric stimulation or high energy shock for treating epilepsy or ventricular fibrillation. It can also be used as part of a cardiac pacemaker/defibrillator system to amplify electrical stimulation and as part of an overall multi-component system.

The device 100, 200 can also be used for the treatment of epilepsy or focalized seizure using intravascular access (small size/discrete efficient tasks) to parts of the brain/nervous system and allow anti-seizure electrical therapy and monitoring to occur. The device 100, 200 can communicate with a central module that is implanted in another area of the patient since it allows reduction in the size of the intra-brain space needed for the device. The device 100, 200 can be activated temporally by the external placement of a handheld device/telemetry communication system.

The device 100, 200 may also be applied to pulmonary intervention and placed in a small bronchiole/airway to monitor local partial pressure/saturations, as well as other local parameters. If placed in several regions, then volume, possible blood flow and pressures can be estimated because of the changes in relative inter-device distances that can be monitored. Other applications within the scope of this invention will be apparent as well.

This invention does not require permanent long lead electrodes to be placed in the vascular system. Those leads are prone to infection, fracture, and other complications. The present invention also eliminates the complex steps and risks of placement of a chronic lead in the patient, and the need for a continuous connection to a direct power supply via a wire. The acute and chronic risks associated with transvenous leads (whether for cardiac pacing or other sensing of cardiac dynamics) are also eliminated.

The intravascular device 100 is preferably from 2 mm-5 cm in diameter, depending on the target site. Accordingly, it can be placed in areas that are not accessible by devices having leads. The device 100, 200 uses the local biologic tissue as the conducting medium for sensing, pacing and defibrillation when used as an antennae and amplifier. The device 100, 200 sends the signal through regular tissue as an analog signal with the frequency and amplitude determined by best characteristics for transmission. It also allows for implantation of ICD or invasive monitoring devices in younger patients or in patients who would not otherwise be considered a candidate for a particular approach because of anatomical abnormalities precluding permanent lead placement. The device 100, 200 is safer and decreases the long term risk of endocarditis and the need for intracardiac extraction of the lead due to failure. Even if the device 100, 200 fails, it can be left where it is without a substantial risk of harm.

The device 100, 200 achieves physiologic sensing and energy delivery using the vasculature (typically venous circulation is safest) as its support structure within the target organ of interest such as the brain and heart. The surrounding blood and biologic tissue can also serve as the conductor; not just as something that energy needs to penetrate, but an actual conductor with its own properties that are exploited. For instance, blood is a transmission medium since it has electrolyte properties and conducting properties that are slightly different from the surrounding tissue. Accordingly, the electrical conducting properties of the blood can be used to send electrical signals to other devices 100, 200 located in other parts of the body.

In addition, the ability to sense both cardiac or neuronal electrical and chemical signals in a vessel allows the ability to sample circulating blood for changes of such material. Devices can be individually tailored to measure chemicals and signals of interest in a dedicated fashion. It can also be used as an adjunct in the treatment of arrhythmias and complex monitoring of biologic signals. It can also be utilized for epilepsy therapy since it is sufficiently small to be implanted in the brain and is able to target the focal scar/electrical site of interest. The venous system serves as the conduit and allows placement of the device 100, 200 in multiple areas without damaging brain tissue or requiring surgery that creates a hole in the skull. The vasculature can be accessed from the femoral veins in the leg or the internal jugular in the neck, or brachial veins in the arm.

More than one device 100, 200 can be provided and networked together, and with an external controller, processor, or the like. A central module can optionally be provided to control and/or correlate operation and exchange of information between the devices 100, 200. Thus, each device 100, 200 can be designed to function independently or as a member of a network of devices 100, 200. The vessel (most likely venous circulation for safety and physiologic reasons) provides the opportunity to form a complex network of sensors/circuits that are small, minimally invasive, and together provide a powerful sensing/stimulation system for intelligent decision-making. Networked devices can be placed in any area of the body where space permits, such as the skin, abdomen and spine.

The device 100, 200 allows bipolar and unipolar sensing of cardiac and neurologic electrical activity, sensing of other physiologic signals, local electrical stimulation (cardiac pacing and defibrillation; neurologic stimulation and seizure therapy), as well as the ability to communicate with other implanted and non-implanted devices via radio frequency and/or optical communication and/or analog signal communication using the body tissue as the conducting medium. Bipolar and unipolar sensing requires two poles or electrodes 108 between which a voltage is applied and an electric field can be generated to stimulate local tissue. The device is about 3 mm-8 cm in length, which allows for good resolution of a very local signal when the two electrodes 108 are close to each other (relative bipolar) and allows recording of far-field activity of surrounding signals when needed.

The combination of local data transmission via biologic tissue coupled with wireless communication enhances the specificity/integrity (reduction of noise/artifact) of the data being transmitted. The device 100 can also be used in an ICD to facilitate defibrillation by drawing the high energy toward the device 100 to better focus the energy field at the heart, thereby amplifying the electrical stimulation on the heart.

The device can generate an electrical stimulation signal that has a variable frequency in terms of pulses, duration of stimulation, as well as amplitude of the voltage, current, and/or interval between stimulations that are suitable for the target site (i.e., the brain, a nerve, the heart, etc.). This is time dependent, but also the energy delivered may be in either a monophasic or biphasic waveform during which the total energy delivered can be altered to be delivered in a variable manner during the pulse. For example, while a pulse may be biphasic, the initial polarity may be positive, then negative, or vice versa. The bulk of energy can be delivered early in the pulse, with the remainder gradually toward the end or vice versa. The variability of the energy delivery is controlled by the controller and power supply of each individual device. The signal generated can be gated or timed to coincide with specific physiologic signals, such as the heart beat or underlying brain electrical activity. The pulses can be synchronized to be delivered at any interval between or simultaneously with the physiologic signal being sensed.

The device 100 is delivered intravascularly by a catheter or fiber optic cabling. The device 100 is positioned near the organ that it is to record data from or stimulate (i.e., the target site or target organ). For example, the device 100 can be placed at the veins on the outside of the heart (cardiac veins). Other target sites include any site outside of the blood vessel, such as placing the extravascular device around a blood vessel to measure its flow or around a nerve bundle (c-clamp or elastic band/ring shape) to sense nerve signals and stimulate the nerve when needed.

The device 100 can be constructed with a collagen matrix, such as described in co-pending application PCT/US2005/015380 entitled "Implantable Bio-Electro-Physiologic Interface Matrix". The device 100 may also be used as a satellite sensor/stimulator or as a controller, such as described in co-pending application PCT/US2005/015379 entitled "Leadless Implantable Cardioverter Defibrillator", filed herewith.

It should be emphasized that the above-described embodiments of the present invention, and particularly, any preferred embodiments, are merely possible examples of implementations, merely set forth for a clear understanding of the principles of the invention. Many variations and modifications may be made to the above-described embodiments of the invention, without departing substantially from the spirit and principles of the invention. All such modifications and variations are intended to be included herein within the scope of this disclosure and the present invention and protected by the following claims.

The invention claimed is:

1. An implantable device comprising:
    a body generally forming an elongated tubular shape and adapted to being implanted in each of an intravascular, extravascular and perivascular space within patient's body;
    an electronic component secured to the body having at least one sensor for sensing electrical or physiological conditions within the patient's body and having at least one electrode for stimulation of tissue at or near the location of implantation wherein the electronic component is configured to output a stimulation through the at least one electrode in response to the sensed electrical air physiological conditions;
    a wireless communication component secured to the body for communicating to and from the device information about the sensed electrical or physiological conditions from the sensor to a second implantable device of similar construction, a controller adapted to coordinate the response to the sensed electrical or physiological conditions with the electronic component and the second device; and
    an induction coil integral to at least a portion of the body for providing power to the electronic component;
    wherein the controller is configured to communicate with the electronic component and the second device to:
    (i) sense with said sensor at a first location where a physiologic stimulus is present and sense at a second location associated with said second device where the physiologic stimulus is absent;
    (ii) apply a first stimulation to said electrode at said first location to treat the physiologic stimulus; and
    (iii) apply a second stimulation by way of the second implantable device at said second location to prevent the physiologic stimulus from reaching the second location; wherein the physiologic stimulus is a seizure.

2. The device of claim 1, wherein said wireless communication component further comprises a wireless transmitter for wireless communication.

3. The device of claim 1, wherein said body comprises a support structure having a pattern.

4. The device of claim 3, wherein the induction coil has a pattern that follows the support structure pattern.

5. The device of claim 1, wherein said device is adapted to being secured at a target intravascular site.

6. The device of claim 1, wherein said device is expandable.

7. The device of claim 6, wherein said device is adapted to be delivered intravascularly to a target site and expanded at the target site to be fixed in position at the target site.

8. The device of claim 1, wherein the device is leadless.

9. The device of claim 1, wherein the body has a stent-like structure.

10. The device of claim 1, wherein said device is adapted to being networked with other extravascular or intravascular devices.

11. The device of claim 1, wherein the seizure is an epileptic seizure.

* * * * *

UNITED STATES PATENT AND TRADEMARK OFFICE
CERTIFICATE OF CORRECTION

PATENT NO. : 8,938,300 B2  
APPLICATION NO. : 11/579529  
DATED : January 20, 2015  
INVENTOR(S) : Spencer Rosero Page 1 of 1

It is certified that error appears in the above-identified patent and that said Letters Patent is hereby corrected as shown below:

Title Page, item (74)

On page 1, the name of the Attorney, Agent or Firm - 'Patent Technologies, LLC; Robert O.Gunderman, Jr.' should read -Patent Technologies, LLC; Robert D. Gunderman, Jr.-

In the Specification

Column 1, line 29, 'to treat a variety if' should read -to treat a variety of-

Column 1, line 30, 'due to the rapid advances' should read -due to rapid advances- Column 1, line 48, 'elsewhere:' should read -elsewhere;-

Column 2, line 26, 'chest are where' should read -chest where-

Column 2, line 33, 'aa well as the limitations' should read -as well as the limitations- Column 3, line 67, 'illustrated in the drawings' should read -as illustrated in the drawings- Column 5, line 20, 'in a manner that' should read -in a manner so that- Column 9, line 5, 'properties of the blood' should read -properties of blood- In the Claims Column 10, lines 39 and 40, claim 1, 'within patient's body' should read -within a patient's body- Column 10, line 47, claim 1, 'sensed electrical air' should read -sensed electrical or- Signed and Sealed this  
Sixteenth Day of February, 2016

Michelle K. Lee  
*Director of the United States Patent and Trademark Office*